United States Patent [19]

Smith et al.

[11] Patent Number: 4,628,041
[45] Date of Patent: Dec. 9, 1986

[54] RHODIUM AND IODINE RECOVERY METHOD

[75] Inventors: Brad L. Smith, Portland; George P. Torrence; Adolfo Aguiló, both of Corpus Christi, all of Tex.

[73] Assignee: Celanese Corporation, New York, N.Y.

[21] Appl. No.: 827,699

[22] Filed: Feb. 10, 1986

[51] Int. Cl.$^4$ .................. B01J 38/68; B01J 27/08; C07C 53/08; C07C 51/12
[52] U.S. Cl. ................................. 502/24; 423/22; 562/519
[58] Field of Search .................. 502/24; 562/519; 423/22

[56] References Cited

U.S. PATENT DOCUMENTS 3,769,326  10/1973  Paulik et al. ............ 562/519
3,887,489  6/1975   Fannin et al. ............ 502/24

FOREIGN PATENT DOCUMENTS 0161874  11/1985  European Pat. Off. ........ 562/519
2146637  4/1985   United Kingdom ........... 562/519

Primary Examiner—P. E. Konopka
Attorney, Agent, or Firm—D. R. Cassady

[57] ABSTRACT

A process for the recovery of rhodium and iodine values and the separation of rhodium from corrosion metal salts in the manufacture of acetic acid by the carbonylation of methanol wherein the reaction mixture contains from about none to about 20 wt % of water, from about 2 to about 20 wt % of alkali metal or alkaline earth metal iodide, methanol, acetic acid, methyl iodide, and carbon monoxide which comprises: (1) removing at least a portion of the reaction solution from the reactor, (2) removing at least a portion of the product acetic acid from the portion in (1) by distillation, (3) adding an excess of methyl acetate to the product depleted material in (2) and heating the resultant mixture to a sufficiently high temperature to convert the methyl acetate to methyl iodide (4) removing the resulting methyl iodide by distillation, (5) continuing to heat the resulting mixture at a temperature and time sufficient to precipitate the rhodium as rhodium iodide, and (6) separating the rhodium iodide and returning it to the reaction mixture.

4 Claims, No Drawings

RHODIUM AND IODINE RECOVERY METHOD

BACKGROUND OF THE INVENTION

A common manufacturing process for acetic acid and related alkyl carboxylic acids is the reaction of a solution of an alcohol of the appropriate carbon skeleton with carbon monoxide in the presence of water, the carboxylic acid, a soluble rhodium salt catalyst, and iodine or iodine containing compound as a reaction promoter preferentially an alkyl iodide of the appropriate carbon skeleton. Examples of this process are described by R. T. Eby and T. C. Singleton in *Applied Industrial Catalysis, Vol.* 1; Academic Press (1983); and U.S. Pat. No. 3,769,329 to Paulik et al.

The catalyst for this process, a soluble rhodium compound, is self-regenerating and is recycled back into the reaction vessel after separation of the product by, for example, a flash distillation or by other similar separation methods.

Due to the corrosive nature of the catalyst solution with operation over an extended period of time, the catalyst solution becomes contaminated with corrosion metal salts; i.e., iron, nickel, molybdenum, chromium, and the like. The presence of these corrosion metal salts increases the production of undesireable by-products such as $CO_2$, $H_2$ and $CH_4$ resulting in a lower raw material efficiency. Decrease catalyst stability and activity can also result from contamination with corrosion metals.

Recovery of the rhodium values has been addressed in U.S. Pat. No. 3,887,489, to Monsanto Company, by Fannin et al.

According to that method, the reaction solution, containing the rhodium catalyst, the iodine containing promoter compound, carbon monoxide, and the undesirable corrosion metal salts, is heated at a temperature of from about 100° C. to about 190° C. at a pressure sufficient to boil off all remaining carbon monoxide for a time sufficient to precipitate the rhodium as an insoluble iodide salt. The patent also describes adding the appropriate alcohol prior to the heating step to convert any hydriodic acid to the corresponding alkyl iodide compound and recovering the alkyl iodide by distillation and condensation during heating. This alkyl iodide can then be reused in the catalyst systems. This process leaves the corrosion metal salts in solution. The insoluble rhodium salts are separated from the soluble corrosion metal salts by decantation, filtration, or the like, and then the rhodium is redissolved by addition of suitable solvents, as for example, water, acetic acid, or a water-acetic acid mixture, and saturating the resulting solution with carbon monoxide.

We have found that this described process is operable in a reaction system that has low concentration of iodide ion, mainly as hydriodic acid as in the traditional methanol carbonylation technology. (U.S. Pat. No. 3,769,329 by Paulik et al.) It does not work in the presence of iodide salts such as alkali metal iodides (e.g. LiI) in significant concentrations and in reaction zones where the water content of the reaction mixture is of the order of 5% or less by weight.

SUMMARY OF THE DISCLOSURE

This invention relates to a method for the recovery and separation from corrosion metals of rhodium and iodine values in a catalyst solution used in an improved carboxylic acid manufacturing process.

In particular, this invention relates to a method for separation of soluble rhodium catalyst from soluble corrosion metal salts in a solution containing from about essentially none to about 20 wt % of water and from about 2 to about 30 wt % of an alkali-metal iodide, an alkyl alcohol, an alkyl carboxylic acid, and carbon monoxide.

According to the method of this invention, the reaction solution treated in the customary manner to remove the desired acid product therefrom, is then especially treated to cause precipitation of the rhodium salt to remove undesirable corrosion metals and recover the iodine values.

By the method of this invention, excess of the appropriate lower-alkyl ester of the carboxylic acid is added to the catalyst solution containing the lower-alkyl iodide, the lower-alkyl ester of the carboxylic acid, lithium iodide, water, hydrogen iodide, carbon monoxide, lower-alkyl alcohol, corrosion metal ions and unrecovered lower-alkyl carboxylic acid. The mixture is heated to a temperature sufficient to convert the lithium iodide to lower-alkyl iodide, the lower-alkyl iodide is removed therefrom and the catalyst now precipitated by the prior art method.

Thus, by the method of this invention, excess methyl acetate is added to the catalyst solution containing, for example, methyl iodide, methyl acetate, lithium iodide, water, hydrogen iodide, carbon monoxide, methanol, corrosion metal ions, and unrecovered acetic acid. The mixture is heated to about 130°-190° C. to convert the LiI to methyl iodide according to the equillibrium represented in equation (I).

Eq. I

Methyl iodide is removed as a vapor phase, condensed, collected, and returned to the reactor. The catalyst solution, now depleted in iodide ion and carbon monoxide will precipitate the rhodium iodide salt by heating in the manner of U.S. Pat. No. 3,887,489.

DETAILED DESCRIPTION OF THE INVENTION

This invention is useful in the manufacture of lower-alkyl carboxylic acids by the reaction of a lower-alkyl alcohol with carbon monoxide in the presence of soluble iodide and rhodium salts as described.

This invention is particularly useful in the manufacture of acetic acid from methanol in the presence of methyl iodide, methyl acetate, an alkali or alkaline earth metal iodide most particularly lithium iodide, water, and soluble rhodium salt.

This invention is most useful when the above reaction is carried out with low concentrations of water; i.e., less than 5 weight % water in the reaction mixture.

A newly discovered method has been found to increase the acetic acid output of a given acetic acid reactor. By this method, it is necessary to substantially increase the iodide ion concentration and to add a substantial quantity of an alkali metal or alkaline earth ion, as for example by the addition of lithium iodide or the like to the reaction mixture. This increased iodide ion concentration in the reaction solution prevents the precipitation of rhodium iodide during catalyst recovery according to the cited prior art method.

The process of manufacture of acetic acid at low water concentrations does not affect the build-up of corrosion metals during long term continuous operation of the carbonylation reaction. Further the added ionic iodide which has been added increases the solubility of the rhodium salts during attempted precipitation of the rhodium in a rhodium recovery and rhodium purifying process. Thus, differential crystalization to separate the rhodium catalyst from the solution containing the corrosion metal ions is made more difficult.

We have found that an equilibrium exists between lithium iodide, methyl acetate, methyl iodide, and lithium acetate as represented by Eq. (I) above. Utilizing this equilibrium, we can reduce the iodide ion concentration in the reaction mixture by adding excess methyl acetate during heating to precipitate the rhodium iodide and to remove the formed methyl iodide by distillation. The thus formed methyl iodide can be reinserted into the manufacturing reaction sequence by, for example, adding it to the reaction vessel or to the flasher (the flasher being the initial product separator in the product stream leading from the reactor), or, more preferrably, by using it as make-up in reactivating the purified rhodium iodide.

According to one exemplification of the process of the present invention, a portion of the reaction solution is removed from the reaction system. This solution is then flash distilled to remove the product. After distillation, excess methyl acetate is added to the solution which is heated to 130°–190° C. for a sufficient time to convert the alkali metal or alkaline earth iodide to methyl iodide. The methyl iodide is removed by distillation and recovered. As a result of the addition of methyl acetate and the equilibrium established among methyl acetate, lithium iodide, methyl iodide and lithium acetate, the distillation removes substantially all of the iodide (e.g. LiI and HI) from the solution as methyl iodide. During the distillation, rhodium salt is precipitated. The mixture is allowed to cool and the solid rhodium salts are removed by decantation, filtration, or other equivalent operative means. The solution containing the corrosion metal salts and lithium acetate is then discarded and the rhodium salt is redissolved in the appropriate alkyl acid, and this solution is then returned to the reaction system.

In another exemplification, after removing the product by flash distillation, methyl acetate is added continuously during distillation of the methyl iodide at from 130°–190° C. Care must be maintained during this modification of the procedure to avoid precipitation of lithium acetate during the distillation. This can be accomplished by maintaining the volume of the solution by the addition of acetic acid during the methyl acetate addition.

EXAMPLE 1

A synthetically created acetic acid solution containing the absolute concentrations of compounds in a typical acetic acid manufacturing run, after flash removal of the acetic acid and carbon monoxide, containing the following materials is prepared.

$H_2O$: <0.1 wt %
$I^-$: 24 wt %
Rhodium: 716 ppm
Lithium: 15000 ppm
Iron: 584 ppm
Chromiun: 196 ppm
Nickel: 604 ppm
Molybdenum: 191 ppm Two gram moles of methyl acetate is added to 200 grams of the above mixture and the mixture is heated to 150° C. for 4 hours in a glass reactor equipped with a pressure release valve, stirrer, and condensor for delivery of condensate. During heating the pressure rose to 80 psig. This distillation valve is then opened and the converted methyl iodide is collected. The reactor is cooled and the solution decanted away from the rhodium iodide residue. The decant contains 14% of the initial charge of iodide ion. Rhodium content of the solid is 86.6% of the initial charge and the supernatent contains the following percentage of the initial charge of the following metal ions.

Rh: 4.8%
Fe: 113%
Cr: 93%
Ni: 93%
Mo: 75%

EXAMPLE 2

A semi-continuous extraction of rhodium iodide from corrosion metals is carried out in the following manner.

An initial charge of solution is heated to 150° C. at 62 PSIG in a Hastelloy B alloy autoclave and allowed to distill. A solution of 80/20 v/v methyl acetate/acetic acid is added to partially replenish the distillate.

At various times during the distillation the distillate is analyzed to determine the concentration of total iodide. After distillation 50 g. of water is added and the mixture heated for 17 hours at 150° C. After heating, the mixture was centrifuged and the supernatent was analyzed for iodide, rhodium and corrosion metals. See Table I.

TABLE I

| Components | Initial Charge | Anal. of distillate after 123 grams is distilled | Anal. of distillate after 231 grams is distilled | Anal. of distillate after 343.7 grams is distilled | Anal. of distillate after 452.7 grams is distilled | Anal. of distillate after 504.2 grams were distilled | Anal. of Reactor after Separation of RhI$_3$ |
|---|---|---|---|---|---|---|---|
| H$_2$O wt % | 2.5 | 2.9 | 2.3 | 2.0 | 1.3 | 1.2 | |
| MeI wt % | | 20.4 | 8.5 | 5.2 | 3.0 | 2.5 | |
| MeOAc wt % | 25.0 | 61.8 | 71.0 | 73.4 | 75.2 | 69.6 | |
| HOAc wt % | 48.4 | 14.9 | 18.2 | 19.4 | 20.4 | 26.7 | |
| LiI wt % | 22.5 | | | | | | 1.26 |
| ppm Rh as RhI$_3$ | 569 | | | | | | 0 |
| ppm Fe as FeI$_2$ | 1127 | | | | | | 1173 |
| ppm Cr as CrI$_3$ | 404 | | | | | | 501 |

Continuous 20/80 v/v HOAc/MeOAc Feed at 2 mL/min rate; 150° C.; 62 psig

TABLE I-continued

Continuous 20/80 v/v HOAc/MeOAc Feed at 2 mL/min rate; 150° C.; 62 psig

| Components | Initial Charge | Anal. of distillate after 123 grams is distilled | Anal. of distillate after 231 grams is distilled | Anal. of distillate after 343.7 grams is distilled | Anal. of distillate after 452.7 grams is distilled | Anal. of distillate after 504.2 grams were distilled | Anal. of Reactor after Separation of RhI$_3$ |
|---|---|---|---|---|---|---|---|
| ppm Ni as NiI$_2$ | 841 | | | | | | 1088 |
| ppm Mo as MoI$_2$ | 158 | | | | | | 128 |
| Total I$^-$ (g) | 42.6 | 22.5 | 8.2 | 5.2 | 2.9 | 1.15 | 2.4 |

HOAc = Acetic Acid; MeOAc = Methyl Acetate
HOAc/MeOAc fed = 469 mL; period = 238 min 1.97 mL/min
Percentage of Rh and corrosion metals initially charged remaining in the reactor solution centrifugate after the reactor solution was centrifuged for 30 minutes: Rh 0.0%, Fe 126%, Ni 132%, Cr 131%, Mo 80%. The corrosion metal percentage is greater than 100% in some cases because some corrosion metals come from the Hastelloy B autoclave.

We claim:

1. A process for the recovery of rhodium and iodine values and the separation of rhodium from corrosion metal salts in the manufacture of acetic acid by the carbonylation of methanol wherein the reaction mixture contains from about none to about 20 wt % of water, from about 2 to about 20 wt % of alkali metal or alkaline earth metal iodide, methanol, acetic acid, methyl iodide, and carbon monoxide which comprises: (1) removing at least a portion of the reaction solution from the reactor, (2) removing at least a portion of the product acetic acid from the portion in (1) by distillation, (3) adding an excess of methyl acetate to the product depleted material in (2) and heating the resultant mixture to a sufficiently high temperature to convert the methyl acetate to methyl iodide (4) removing the resulting methyl iodide by distillation, (5) continuing to heat the resulting mixture at a temperature and time sufficient to precipitate the rhodium as rhodium iodide, and (6) separating the rhodium iodide and returning it to the reaction mixture.

2. The process of claim 1 wherein after the methyl acetate is added, the mixture is heated to from about 130°–190° C. to convert the methyl acetate to methyl iodide.

3. The process of claim 2 wherein the rhodium iodide is precipitated at a temperature of from about 100°–190° C.

4. A process for the recovery of rhodium and iodine values and the separation of rhodium from corrosion metal salts in the manufacture of acetic acid by the carbonylation of methanol wherein the reaction mixture contains from about none to about 20 wt % of water, from about 2 to about 20 wt % of lithium iodide, methanol, acetic acid, methyl iodide, and carbon monoxide which comprises: (1) removing at least a portion of the reaction solution from the reactor, (2) removing at least a portion of the product acetic acid from the portion in (1) by distillation, (3) adding an excess of methyl acetate to the product depleted material in (2) and heating the resultant mixture to from about 130°–190° C. continuously removing the resulting methyl iodide by distillation, (5) continuing to heat the resulting mixture at from about 100°–190° C. for a time sufficient to precipitate the rhodium as rhodium iodide, and (6) separating the rhodium iodide and returning it to the reaction mixture.

* * * * *